US006476062B2

(12) United States Patent
Chu et al.

(10) Patent No.: US 6,476,062 B2
(45) Date of Patent: Nov. 5, 2002

(54) CHEMOKINE RECEPTOR ANTAGONISTS

(75) Inventors: Min Chu, Basking Ridge; Ronald A. Mierzwa, Bloomfield; Joseph Terracciano, Scotch Plains; Mahesh G. Patel, Verona, all of NJ (US)

(73) Assignee: Schering Corporation, Kenilworth, NJ (US)

( * ) Notice: Subject to any disclaimer, the term of this patent is extended or adjusted under 35 U.S.C. 154(b) by 16 days.

(21) Appl. No.: 09/815,853

(22) Filed: Mar. 23, 2001

(65) Prior Publication Data
US 2002/0128307 A1 Sep. 12, 2002

Related U.S. Application Data
(60) Provisional application No. 60/193,331, filed on Mar. 30, 2000.

(51) Int. Cl.$^7$ ................... C07D 207/04; A61K 31/40
(52) U.S. Cl. ........................... 514/425; 548/544
(58) Field of Search ............................ 548/544; 514/425

(56) References Cited

U.S. PATENT DOCUMENTS 5,759,842 A * 6/1998 Dombrowski et al. ... 435/252.1
5,951,974 A    9/1999 Gilbert et al.
6,124,327 A * 9/2000 Silverman et al. .......... 514/352

FOREIGN PATENT DOCUMENTS

EP    0 809 996 A2    12/1997

OTHER PUBLICATIONS

Singh, S.B. et al (1998): Tetrahedron Letters; vol. 39, 2243–2246.*

M.P. Singh, LL–49F233a, a Novel Antibiotic Produced by an Unknown Fungus: Biological and Mechanistic Activities, The Journal of Antibiotics, vol. 51(12), 1998, pp. 1109–1112.

* cited by examiner

Primary Examiner—Joseph K. McKane
Assistant Examiner—Golam M. M. Shameem
(74) Attorney, Agent, or Firm—Thomas D. Hoffman

(57) ABSTRACT

Novel tetramic acid-type compounds isolated from a CCR-5 active complex produced by fermentation under controlled conditions of a biologically pure culture of the microorganism, *Chaetomium globosum* Kunze SCH 1705, ATCC 74489., pharmaceutical compositions containing the compounds and the use of the CCR-5 antagonist compounds and compositions to treat HIV-1 infections in humans are disclosed.

8 Claims, No Drawings

CHEMOKINE RECEPTOR ANTAGONISTS

This application claims benefit of No. 60/193,331 Mar. 30, 2000.

BACKGROUND OF THE INVENTION

This invention relates to novel tetramic acid-type compounds, pharmaceutical compositions containing them and their use as CCR-5 antagonists to treat Human Immunodeficiency Virus-1 ("HIV-1") infections in humans. The compounds of this invention were isolated from a CCR-5 active complex which is produced by fermentation, under controlled conditions, of a biologically pure culture of the microorganism, *Chaetomium globosum* Kunze SCH 1705, ATCC 74489.

M. P. Singh et al., *The Journal of Antibiotics,* December 1998, Vol. 51, No. 12, p 1109–1112 disclosed novel antibiotics produced by an unknown fungus and including LL-49F233d containing an N-methyl tetramic acid moiety attached to a bicyclic hydrocarbon skeleton. These antibiotics are disclosed to be active against vancomycin and methicillin-resistant bacteria but no anti-HIV-1 activity is disclosed. S. B. Singh et al., *Tetrahedron Letters,* 39 (1998) 2243–2246 disclose that the N-methyl tetramic acid derivatives, equisetin and phomasetin, which are isolated from microbial extracts, are inhibitors of HIV-1 integrase. Neither reference discloses the compounds of the present invention.

A-M. Vandamme et al., *Antiviral Chemistry & Chemotherapy,* 9:187–203 (1998) disclose current clinical treatments of HIV-1 infections in man including at least triple drug combinations or so-called Highly Active Antiretroviral Therapy ("HAART"); HAART involves various combinations of nucleoside reverse transcriptase inhibitors ("NRTI"), non-nucleoside reverse transcriptase inhibitors ("NNRTI") and HIV protease inhibitors ("PI"). In compliant drug-naive patients, HAART is effective in reducing mortality and progression of HIV-1 to AIDS. However, these multidrug therapies do not eliminate HIV-1 and long-term treatment usually results in multidrug resistance. Development of new drug therapies to provide better HIV-1 treatment remains a priority.

The CCR5 chemokine receptor has been identified as co-receptor for HIV-1 entry in cells. Therefore, CCR5 antagonists that interfere with the interaction between the CCR5 receptor and HIV-1 can block HIV-1 entry into the cell.

The global health crisis caused by HIV-1, the causative agent of Acquired Immunodeficiency Syndrome (AIDS), is unquestioned, and while recent advances in drug therapies have been successful in slowing the progression of AIDS, there is still a need to find new drug therapies to control HIV-1 infections.

SUMMARY OF THE INVENTION

The present invention embraces *Chaetomium globosum* Kunze SCF 1705, ATCC 74489 and mutants and variants thereof having the identifying characteristics of *Chaetomium globosum* Kunze.

Another aspect of the invention provides CCR5-active complex produced by cultivating a biologically pure strain of *Chaetomium globosum* Kunze SCF 1705 having the identifying characteristics of *Chaetomium globosum* Kunze ATCC 74489 in a pH and temperature controlled medium having assumable sources of carbon and nitrogen under submerged aerobic conditions until a composition of matter having substantial anti HIV-1 activity is produced.

The present invention is also directed to three components of the CCR5-active complex, i.e. compounds represented by formulas I, II and III.

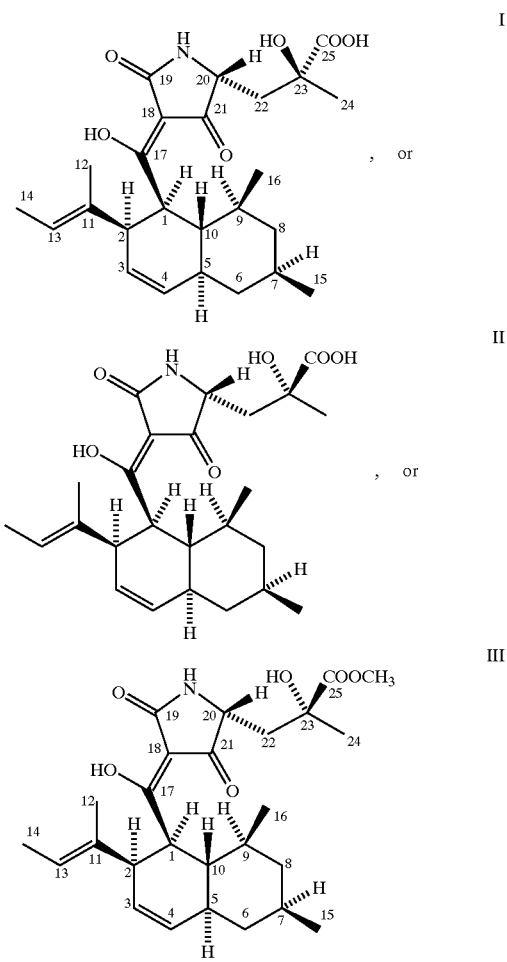

in substantially chemically pure form, or a pharmaceutically acceptable salt thereof.

The present invention relates to methods of using compounds of formulas I, II or III—which are CCR5 antagonists—as monotherapy or in association with pegylated interferon-alfa to treat patients having immunodeficiency virus type-1("HIV-1") infections.

The present invention also relates to methods of treating patients having HIV-1 infections by administering a therapeutically effective amount of HAART in association with a therapeutically effective amount of a compound of formulas I, II or III sufficient to lower HIV-1-RNA.

The present invention also relates to methods of treating patients having HIV-1 infections by administering a therapeutically effective amount of pegylated interferon-alfa in association with a therapeutically effective amount of a compound of formulas I, II or III sufficient to lower HIV-1-RNA.

The present invention also provides a method of treating pediatric patients having HIV-1 infections which comprises administering a therapeutically effective amount of pegylated interferon-alfa in association with a therapeutically effective amount of a CCR5 antagonist represented by the structural formula I or II or III.

The present invention also provides a method of treating patients co-infected with HIV-1 and HCV which comprises administering a therapeutically effective amount of pegylated interferon-alfa in association with a therapeutically effective amount of ribavirin and a therapeutically effective amount of HAART and a therapeutically effective amount of a CCR5 antagonist represented by the structural formula I or II or III.

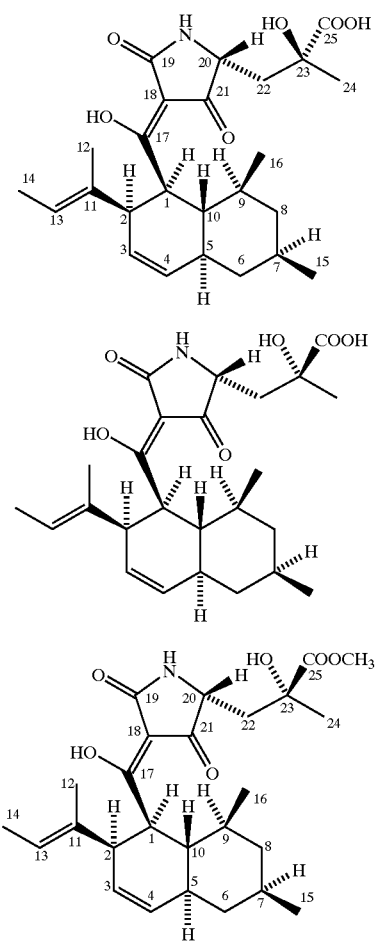

in substantially chemically pure form, or a pharmaceutically acceptable salt thereof.

DETAILED DESCRIPTION OF THE INVENTION

The Microorganism

The microorganism used for the production of CCR5-active complex and the compounds represented by formulas I, II and III is a biologically pure culture of *Chaetomium globosum* Kunze SCF 1705, ATCC 74489.

A viable culture of this microorganism has been deposited (on Apr. 21, 1999) in the collection of the American Type Culture Collection (ATCC) 10801 University Blvd., Manassas, Va. 20110-2209 where it has been assigned the accession number ATCC 74489. Should the deposited culture become lost, destroyed or nonviable during the longer of thirty (30) year period from the date the culture was deposited or the five (5) year period after the last request for the deposited culture, or the effective life of the patent which issues from this application, the culture will be replaced, upon notice, to applicants or assignee(s) of this application. Subcultures of *Chaetomium globosum* Kunze SCF 1705, ATCC 74489 are available during pendency of this application to one determined by the Assistant Commissioner for Patents and Trademarks to be entitled under 37CFR 1.14 and 35USC 122 and will be available to the public without restriction once a U.S. Patent based on this application is granted. Use of the microorganism is dependent upon the U.S. Patent laws.

The producing microorganism was isolated from a leaf sample of evergreen plants collected in Tuscan Ariz. as an unidentified fungus. It has been characterized and found to have the microscopic, macroscopic and whole cell hydrolysia properties of the genus Chaetomium.

Description of the producing strain *Chaetomium globosum* Kunze SCF 1705, ATCC 74489

Morphology

Morphological observations of the producing strain of *Chaetomium globosum* SCF 1705 were made on the following agar's Standardized description of SNA (Synthetischer nährstoffarmer agar), formulated as follows:

$KH_2PO_4$ 1.0 g
$KNO_3$ 1.0 g
$MgSO_4 \cdot 7H2O$ 0.5
KCl 0.5 g
Glucose 0.2 g
Saccharose 0.2 g
Agar 20.0 g
$dH_2O$ 1000 mL Pieces of sterile filter paper (about 5 cm round) placed on the surface of the agar after it has solidified.

Colonies growing 50–70 mm diam. on SNA after 10 days at room temperature (in a 12 hr dark: 12 hr light cycle, with the light a mixture of near UV and fluorescent), comprised of perithecia (sexual fruiting bodies) scattered over much of the surface, concentrated near the inoculum and around the edge of the filter paper, then in vague concentric rings outwards, with little aerial mycelium and the submerged mycelium unpigmented and inconspicuous. Perithecia superficial, easily removed from the substrate, single, scattered or in continuous masses, olivaceous in superficial view, but actually black and covered with a dense layer of straight and coiled greyish hyphae that project 300–400 μM beyond the perithecial wall, resulting in the olivaceous color and hirsute appearance, 700–1250 μM tall and 700–1100 μM wide including the superficial hairs, about 300–600× 125–350 μM excluding the superficial hyphae. Peridium (perithecial wall) black in surface view, comprised of a textura epidermoidea (jig-saw puzzle like arrangement) of brown cells 2.5–4 μM wide, with slightly uneven, slightly thickened walls. Hyphae covering peridium of two types, both with scattered septa; the first formed are straight and emerged from the base of the perithecium; the second formed are helically coiled, 2.5–3.5 μM wide, with evenly thickened, slightly thickened walls covered with minute crystals, resulting in a spiny to warty surface appearance. Asci (structures containing spores) not seen, assumed to be deliquescent. Ascospores (sexual spores) 9.5–10.5×8–9 μM, ellipsoidal to slightly lemon shaped, olivaceous, smooth-walled, walls slightly thickened, with a pore about 1 μM wide at one end (See FIG. 9). Ascospores holding together in horn-like, black masses called chirrhi, up to 300 μM long and 50–125 μM wide.

The term "pharmaceutically acceptable salts thereof" as used herein refers to salts formed by contacting compounds of formulas I–III with pharmaceutically acceptable bases.

The pharmaceutically acceptable bases found suitable for use in the present invention are those that form pharmaceutically acceptable salts of the compounds of formulas I, II or III and include suitable organic and inorganic bases. Suitable organic bases include primary, secondary and tertiary alkyl amines, alkanolamines, aromatic amines, alkylaromatic amines and cyclic amines. Exemplary organic amines include the pharmaceutically acceptable bases selected form chloroprocaine, procaine, piperazine, glucamine, N-methylglucamine, N,N-dimethyl glucamine ethylenediamine, diethanolamine, diisopropylamine, diethylamine, N-benzyl-2-phenylethylamine, N-N'-dibenzylethylenediamine, choline, clemizole, tris (hydroxymethyl)-aminomethane, or D-glucosamine. The preferred organic bases include N-methyl glucamine ("NMG"), diethanolamine, and tris(hydroxymethyl) aminomethane ("TRIS").

It has been reported that the CCR5 gene plays a role in resistance to HIV infection. HIV infection begins by attachment of the virus to a target cell membrane through interaction with the cellular receptor CD4 and a secondary chemokine co-receptor molecule, and proceeds by replication and dissemination of infected cells through the blood and other tissue. There are various chemokine receptors, but for macrophage-tropic HIV, believed to be the key pathogenic strain that replicates in vivo in the early stages of infection, the principal chemokine receptor required for the entry of HIV-1 into the cell is CCR5. Therefore, interfering with the interaction between the viral receptor CCR5 and HIV can block HIV-1 entry into the cell.

The terms "CCR5 antagonist compound" and "CCR5 antagonists" as used herein mean any compound that interfers with the interaction between the viral receptor CCR5 and HIV-1 to block entry of HIV-1 into the cell. Assays, e.g., the CCR5 Membrane Binding Assay, the HIV-1 Entry and the HIV-1 Entry Replication Assays, inter alia, are presented herein after to identify a compound as a CCR5 antagonist and to determine its CCR5 antagonist activity.

The present method of treating patients having HIV-1 infections comprises administrating a therapeutically effective amount of a CCR5 antagonist compound represented by structural formula I or II or III in association with a therapeutically effective amount of pegylated interferon-alfa, or in association with a therapeutically effective amount of at least one of ribavirin, interleukin-2("IL-2"), interleukin-12("IL-12"), and pentafuside alone or in combination with an anti-HIV-1 therapy, especially, HAART in accordance with good clinical practice to minimize HIV-1-RNA plasma levels. See for example A-M. Vandamme et al., in *Antiviral Chemistry & Chemotherapy*, 9:187–203 (1998) and "Drugs for HIV Infection" in *The Medical Letter*, Vol. 39 (Issue 1015) Dec. 5, 1997, pages 111–116. In a preferred aspect of the present invention, the combination of a pegylated interferon alpha and a CCR5 antagonist of formulas I to III is administered to a patient infected with HIV-1, or co-infected with HIV-1 and HCV, in association with ribavirin and HAART. It is a special feature of the present invention that each of pegylated interferon alpha, the CCR5 antagonists of formulas I to III and the components of HAART has a different mechanism of action in treating HIV-1. It is another special feature of the present invention that the pegylated interferon alpha and the CCR5 antagonists of formulas I to III do not cause cross-resistance with each other or with the components of HAART. The initiation of the administration of a therapeutically effective amount of the combination of a pegylated interferon alpha, ribavirin, and a CCR5 antagonist compound represented by structural formula I or II or III and HAART may occur before, after or concurrently with administering a therapeutically effective amount of combination of a pegylated interferon-alfa and a CCR5 antagonist compound represented by structural formula I or II or III in accordance with the present invention. In an embodiment of the present invention, the method of treating patients having HIV-1 infections comprises two treatment time periods. In the first treatment time period, a combination of a therapeutically effective amount of pegylated interferon-alfa and a CCR5 antagonist compound represented by structural formula I or II or III is administered for a first treatment time period sufficient to lower HIV-1-RNA plasma levels, preferably by a power of 10, more preferably by at least two powers of ten, i.e., at least $10^2$, lower than the initial HIV-1-RNA plasma level. In the second treatment time period, the method entails continuing the administration of a therapeutically effective amount of a combination of pegylated interferon-alfa in association a CCR5 antagonist compound represented by structural formula I or II or III and a therapeutically effective amount of HAART in accordance with good clinical practice to minimize HIV-1-RNA plasma levels. A-M. Vandamme et al., *Antiviral Chemistry & Chemotherapy*, 9:187–203 (1998) disclose current clinical treatments of HIV-1 infections, including when to start multidrug therapy and which drugs to combine. The triple drug therapy may include two NRTIs and one PI, but there are many issues to be considered in the choice of the precise HAART for any patient. See for example, Tables 1 & 2 in A-M. Vandamme et al., listed hereinabove.

The term "patients having HIV-1 infections" as used herein means any patient—including a pediatric patient—having HIV-1 infection and includes treatment-naive patients and treatment-experienced patients having the HIV-1 infection as well as treatment-naive patients and treatment-experienced patients co-infected with the HIV-1 and hepatitis C virus ("HCV").

The term "pediatric patient" as used herein means a patient below the age of 17, and normally includes those from birth to 16 years of age.

The term "treatment-naive patients" as used herein means patients having HIV-1 or co-infected with the HIV-1 and HCV who have never been treated with any anti-retroviral drugs, e.g., NRTI, NNRTI, PI or any interferon, including but not limited to interferon-alfa, or pegylated interferon alfa.

The term "treatment-experienced patients" as used herein means those patients having HIV-1 or co-infected with the HIV-1 and HCV who have initiated some form of anti HIV therapy including, but not limited to HAART or some form of anti-HCV therapy, including but not limited to interferon-alfa, pegylated interferon alfa or ribavirin.

The term "patients having hepatitis C infections" as used herein means any patient—including a pediatric patient—having hepatitis C and includes treatment-naive patients having hepatitis C infections and treatment-experienced patients having hepatitis C infections as well as those pediatric, treatment-naive and treatment-experienced patients having chronic hepatitis C infections.

These patients having hepatitis C include those who are infected with mutiple HCV genotypes including type 1 as well as those infected with,e.g., HCV genotypes 2, 3, 4, 5 and/or 6 and other possible HCV genotypes.

The term "treatment-naive patients having hepatitis C infections" as used herein means patients with hepatitis C who have never been treated with ribavirin or any interferon, including but not limited to interferon-alfa, or pegylated interferon alfa.

The term "treatment-experienced patients having hepatitis C infections" as used herein means patients with hepatitis C who have been treated with ribavirin or any interferon, including but not limited to interferon-alfa, or pegylated interferon alfa, including relapsers and non-responder.

The term "relapsers" as used herein means treatment-experienced patients with hepatitis C who have relapsed after initial response to previous treatment with interferon alone, or in combination with ribavirin.

The term "non-responders" as used herein means treatment-experienced patients with hepatitis C who have not responded to prior treatment with any interferon alone, or in combination with ribavirin.

When the pegylated interferon-alfa administered is a pegylated interferon alfa-2b, the therapeutically effective amount of pegylated interferon alfa-2b administered during the treatment in accordance with the present invention, including in first and second treatment time periods, is in the range of about 0.1 to 9.0 micrograms per kilogram of pegylated interferon alfa-2b administered per week, in single or divided doses, preferably once a week (QW) or twice a week (BIW), preferably in the range of about 0.1 to about 9.0 micrograms per kilogram of pegylated interferon alfa-2b administered once a week (QW) or in the range of about 0.05 to about 4.5 micrograms per kilogram of pegylated interferon alfa-2b administered twice a week (BIW), or is in the range of about 0.5 to about 3.0 micrograms per kilogram of pegylated interferon alfa-2b administered per week, preferably in the range of about 0.5 to about 3.0 micrograms per kilogram of pegylated interferon alfa-2b administered once a week (QW) or in the range of about 0.25 to about 1.5 micrograms per kilogram of pegylated interferon alfa-2b administered twice a week, or is in the range of about 0.75 to about 1.5 micrograms per kilogram of pegylated interferon alfa-2b administered per week, most preferably is in the range of about 0.75 to about 1.5 micrograms per kilogram of pegylated interferon alfa-2b administered once a week or about 0.375 to about 0.75 micrograms per kilogram of pegylated interferon alfa-2b administered twice a week.

When the pegylated interferon-alfa administered to pediatric patients is a pegylated interferon alfa-2b, the therapeutically effective amount of pegylated interferon alfa-2b administered during the treatment in accordance with the present invention, including in first and second treatment time periods is in the range of about 0.1 to 9.0 micrograms per kilogram of pegylated interferon alfa-2b administered per week, in single or divided doses, preferably once a week (QW) or twice a week (BIW), more preferably about 0.1 to about 9.0 micrograms per kilogram of pegylated interferon alfa-2b administered once a week (QW), or about 0.05 to about 4.5 micrograms per kilogram of pegylated interferon alfa-2b administered per week, in single or divided doses, preferably once a week (QW) or twice a week (BIW), more preferably about 0.05 to about 4.5 micrograms per kilogram of pegylated interferon alfa-2b administered once a week, or preferably about 0.75 to about 3.0 micrograms per kilogram of pegylated interferon alfa-2b administered in single or divided doses, preferably once a week (QW) or twice a week (BIW), more preferably about 0.75 to about 3.0 micrograms per kilogram of pegylated interferon alfa-2b administered once a week or about 0.375 to about 1.5 micrograms per kilogram of pegylated interferon alfa-2b administered twice a week, and most preferably about 2.25 to about 2.6 micrograms per kilogram of pegylated interferon alfa-2b administered once a week or about 1.1 to about 1.3 micrograms per kilogram of pegylated interferon alfa-2b administered twice a week (BIW).

When the pegylated interferon-alfa administered is a pegylated interferon alfa-2a, the therapeutically effective amount of pegylated interferon alfa-2a administered during the treatment in accordance with the present invention, including in first and second treatment time periods, is in the range of about 50 micrograms to about 500 micrograms once a week ("QW"), preferably about 200 micrograms to about 250 micrograms QW or the effective amount is in the range of about 50 micrograms to about 250 micrograms twice a week, preferably about 100 micrograms to about 125 micrograms twice a week.

When the pegylated interferon-alfa administered to a pediatric patient is a pegylated interferon alfa-2a, the therapeutically effective amount of pegylated interferon alfa-2a administered during the treatment in accordance with the present invention, including in first treatment time period is in the range of about 50 micrograms to about 500 micrograms once a week ("QW"), preferably about 300 micrograms to about 375 micrograms QW or the therapeutically effective amount of pegylated interferon alfa-2a administered to a pediatric patient is in the range of about 50 micrograms to about 250 micrograms twice a week, preferably about 150 micrograms to about 190 micrograms once a week.

Ribavirin is administered to the patient in association with pegylated interferon-alfa, that is, before, after or concurrently with the administration of the pegylated interferon alfa. The pegylated interferon-alfa dose is preferably administered during the same period of time that the patient receives doses of ribavirin. The amount of ribavirin administered concurrently with the pegylated interferon-alfa is from about 400 to about 1600 mg per day, preferably about 600 to about 1200 mg/day or about 800 to about 1200 mg day and most preferably about 1000 to about 1200 mg/kg a day. The pegylated interferon-alfa dose is also preferably administered to the pediatric patient during the same period of time that such patient receives doses of ribavirin. The amount of ribavirin administered to the pediatric patient concurrently with the pegylated interferon-alfa is from about 8 to about 15 mg per kilogram per day, preferably about 8, 12 or 15 mg per kilogram per day, in divided doses.

Pegylated interferon-alfa formulations are not effective when administered orally, so the preferred method of administering the pegylated interferon-alfa is parenterally, preferably by subcutaneous, IV, or IM, injection. Ribavirin may be administered orally in capsule, tablet or liquid form in association with the parenteral administration of pegylated interferon-alfa. Of course, other types of administration of both medicaments, as they become available are contemplated, such as by nasal spray, transdermally, by suppository, by sustained release dosage form, and by pulmonary inhalation. Any form of administration will work so long as the proper dosages are delivered without destroying the active ingredient.

Fermentation of the Microorganism

The CCR-5 active complex of this invention is produced when the producing microorganism, MER-229, is grown in an aqueous nutrient medium under submerged aerobic conditions at a temperature of about 240° C. to 37° C., preferably at from 24° C. to 35° C., and at a pH of from about 6.5 to 8.0 with agitation until substantial CCR-5 activity is imparted to the medium. Temperature studies indicate that the organism grows rapidly at about 24° C. Therefore, the fermentation is preferably conducted employing a single temperature pattern of about 24° C. for a period of about 48 to about 144 hours preferably about 120 hours in flasks.

The growth of the organism (packed cell volume, pH and residual glucose concentration are determined intermittently. During the course of the fermentation, production of the CCR-5 active complex was monitored by the CCR-5 assay.

As nutrient medium, there is employed any suitable medium containing a source of carbon, for example an assimilable carbohydrate, and a source of nitrogen, for example an assimilable nitrogenous or proteinaceous material and various mineral salts.

The medium employed for the fermentation contained proteose peptone, yeast extract, cerelose and soy grits as the major sources of nitrogen and carbon, respectively. Under these conditions, the microorganism, MER-229, produced active components as determined by monitoring the fermentation using the CCR-5 assay.

The foregoing media are exemplary of the nutrients utilized by MER-229 to produce active components. However it is obvious to those trained in fermentation science that a wide range of nutrients obtained from a number of suppliers may be substituted for the foregoing, and that generally good growth and production can be obtained, such nutrients being the functional equivalent to those set forth herein.

The fermentation is generally conducted by initially sterilizing the fermentation medium prior to the addition of the inoculum. Prior to sterilization, the pH of the medium is usually adjusted to 7.

The fermentation was initiated by addition of the inoculum to the broth. Generally, inoculum volume is between 3.5 to 7.0% of total broth volume. The inoculum is prepared by addition of a sample of 5% inoculum of the frozen whole broth of the producing culture to an appropriate germination medium. A particularly preferred germination medium in grams/liter comprises proteus peptone #3, 5.0; sodium chloride 5.0; cerelose, 20.0; yeast extract, 3.0; soy grits, 5.0 and sodium potassium phosphate (monobasic) 5.0. The inoculum stage of the fermentation usually requires from 24 to 120 hours with 72–96 hours being preferred and is generally conducted at about 24° C. with agitation (250 rpm). A 5% inoculum of this culture is transferred to the same germination medium and grown as described hereinabove. Inoculum developed in this manner is transferred to the fermentation medium. A particularly preferred fermentation medium comprises 10 g/L of neopeptone, 40 g/L of cerelose and 5 g/L of calcium carbonate. The fermentation stage usually requires from 96 to 144 hours with 120 hours being preferred and is generally conducted at about 24° C. with agitation (250 rpm). The pH of the solution is adjusted to 7. An antifoam agent such as Antifoam B (Dow Corning) is added to the medium to control foam, if necessary. An active complex as detected by the CCR-5 assay is produced.

Isolation of the CCR-5 Active Compounds

As a first step in the isolation process, a conventional ethyl acetate extraction at harvest pH (6.5–7.2) cannot be utilized to extract Sch 210791 (I), Sch 210792 (II) and Sch 213766 (III) from the fermentation broth. Solid phase extraction (SPE) methodology was originally applied on small scale using DZC-18 (Diazem) packing material. Further evaluation indicated that I, II and III could be extractable with ethyl acetate under acidic condition (pH=2). The fermentation broth (4 liter) was adjusted with concentrated hydrochloric acid (12 N, 37%) to pH 2, then extracted with 12 liter of ethyl acetate. After removal of solvent under reduced pressure, the crude extract (8 g) was partitioned with a biphasic solvent system (hexane: ethyl acetate: methanol: water with 5% acetic acid, 8:2:5:5). The CCR-5 active complex from upper phase portion (800 mg) was chromatographed by normal phase HPLC (YMC semi-preparative PVA-Sil column 30×250 mm with guard 30×75 mm, S-5, 2% MeOH in n-butyl chloride isocratic, 24 mL/min, UV=295 nm) to obtain pure I (6 mg) and III (20 mg) and enriched complex. The enriched complex was further purified by reverse phase HPLC (YMC semi-preparative ODS column, 20×250 mm with a guard column 20×50 mm, S-5, 70–100% acetonitrile in water with a linear gradient in 15 min, 12 mL/min, UV=220 nm) to afford pure II (5 mg).

Physico-Chemical Properties of Compounds I, II, and III

Both compounds I & II were crystallized with acetone/methylene chloride (1:1) to form crystalline solids. However, compound III was obtained as a gummy material after removal of solvent from HPLC purification and could not be crystallized with several solvent systems. All three compounds were soluble in acetone, ethyl acetate, acetonitrile, methylene chloride and methanol, insoluble in hexane and water. These compounds were negative in ninhydrin test and positive in Rydon test. The physico-chemical properties of the compounds are summarized in Table I.

Structure Determination of Compounds of Formulas I, II & III

Structure elucidation of compounds of formulas I, II & III was accomplished based on analyses of spectroscopic data, including UV, IR, MS, $^1$H and $^{13}$C NMR experiments. $^1$H and $^{13}$C NMR spectral data are shown in Table 2 and 3. Assignments of the protons and carbons were established by correlated spectroscopy (COSY) and attached proton test (APT) experiments, respectively. Protons to the relevant carbons were assigned by heteronuclear correlated (HETCOR) experiments. Connections of proton and carbon were made based on heteronuclear multiple bond correlation (HMBC), heteronuclear multiple quantum coherence (HMQC) and selective insensitive nuclear enhanced by polarization transfer (SINEPT) experiments. The relative stereochemistry was determined by two-dimensional nuclear Overhauser effect spectroscopy (NOSEY). The proposed structure and relative stereochemistry of these compounds were further confirmed by X-ray crystallographic data analyses of compound II, which is shown in Table 4. All three compounds belong to tetramic acid family of compounds with a linkage of a hydrophobic bicyclic moiety. Compounds I & II are stereoisomers at chiral center C-23 position. Compound III is a methyl ester of the carboxy group at C-25 position.

TABLE 1

Physico-Chemical Properties of Compounds of Formulas I, II & III

| | I | II | III |
|---|---|---|---|
| M.P. ° C. | 126–128 | 149–150 | —[1] |
| ESI-MS (m/z)[2] | 446 (MH + H)+ | 446 (M + H)+ | 460 (M + H)+ |
| Elemental Analysis Calcd: | $C_{25}H_{35}NO_6$ C67.42, H7.87, N3.15 | $C_{25}H_{35}NO_6$ C67.42, H7.87, N.315 | $C_{26}H_{37}NO_6$ C67.97, H8.06, N3.05 |
| Found: | C68.23, H7.98, N3.11 | C66.95, H7.51, N3.58 | C67.11, H7.88, N3.67 |
| [ ]$^{24}$$_D$ (Acetone) | +127.5° | +40.0° | +33.3° |

TABLE 1-continued

Physico-Chemical Properties of Compounds of Formulas I, II & III

| | I | II | III |
|---|---|---|---|
| UV(MeOH) $_{max}$ nm | 220, 290 | 220, 295 | 220, 295 |
| IR (Kbr) $_{max}$ cm$^{-1}$ | 3390, 1725 1650, 1595, 1440. | 3436, 1710 1645, 1578, 1447. | 3407, 1736 1655, 1602, 1456. |

[1]Compound III appears to be a gum-like soft solid material probably due to the presence of two isomeric form (enol-ketone equilibration).
[2]Electrospray ionization mass spectral data.

TABLE 2

$^1$H NMR Data of Compounds of Formulas I, II & III[a]

| Proton # | I | II | III |
|---|---|---|---|
| 1 | 3.95 dd (8.0, 7.0)[b] | 3.94 dd (8.0, 7.0) | 3.95 dd (8.0, 7.0) |
| 2 | 3.01 dt (8.0, 1.0, 1.0) | 3.00 dt (8.0, 1.0, 1.0) | 3.00 dt (8.0, 1.0, 1.0) |
| 3 | 5.67 br.s | 5.66 br.s | 5.66 br.s |
| 4 | 5.67 br.s | 5.66 br.s | 5.66 br.s |
| 5 | 1.85 m | 1.85 m | 1.82 m |
| 6 | 0.93, 1.90 m | 0.95, 1.91 m | 0.95, 1.90 m |
| 7 | 1.62 m | 1.63 m | 1.63 m |
| 8 | 0.82, 1.64 m | 0.83, 1.66 m | 0.83, 1.66 m |
| 9 | 1.38 m | 1.39 m | 1.39 m |
| 10 | 1.40 m | 1.40 m | 1.40 m |
| 11 | — | — | — |
| 12 | 1.58 br.s | 1.57 br.s | 1.59 br.s |
| 13 | 5.20 dq (6.5, 1.0) | 5.19 dq (6.5, 1.0) | 5.19 dd (6.5, 1.0) |
| 14 | 1.51 br.d (6.5) | 1.50 br.d (6.5) | 1.50 br.d (6.5) |
| 15 | 0.92 d (6.5) | 0.91 d (6.5) | 0.91 d (6.5) |
| 16 | 0.84 d (6.5) | 0.85 d (6.5) | 0.84 d (6.5) |
| 17 | — | — | — |
| 18 | — | — | — |
| 19 | — | — | — |
| 20 | 4.10 dd (10.0, 2.5) | 3.80 dd (10.0, 2.5) | 4.04 dd (10.0, 2.5) |
| 21 | — | — | — |
| 22 | 1.90 dd (14.0, 10.0) 2.22 dd (14.0, 2.5) | 1.75 dd (14.0, 10.0) 2.50 dd (14.0, 2.5) | 1.72 dd (14.0, 10.0) 2.45 dd (14.0, 2.5) |
| 23 | — | — | — |
| 24 | 1.49 s | 1.49 s | 1.46 s |
| 25 | — | — | — |
| 25-OCH$_3$ | — | — | 3.77 s |

[a]Measured at 400 MHz in acetone-d$_6$, chemical shifts in ppm from TMS.
[b]Coupling constants in Hz.

CCR5 Membrane Binding Assay

A high throughput screen utilizing a CCR5 membrane binding assay identifies inhibitors of RANTES binding. This assay utilizes membranes prepared from NIH 3T3 cells expressing the human CCR5 chemokine receptor which have the ability to bind to RANTES, a natural ligand for the receptor. Using a 96-well plate format, membrane preparations are incubated with $^{125}$I-RANTES in the presence or absence of compound for one hour. Compounds are serially diluted over a wide range of 0.001 ug/ml to 1 ug/ml and tested in triplicates. Reaction cocktails are harvested through glass fiber filters, and washed thoroughly. Total counts for replicates are averaged and data reported as the concentration required to inhibit 50 percent of total $^{125}$I-RANTES binding. Compounds with potent activity in the membrane binding assay are further characterized in secondary cell-based HIV-1 entry and replication assays.

Activity of Compound of Formula II in CCR5 Membrance Binding Assay

The activity of the compound of formula II was evaluated in the CCR5 membrane binding assay. The assay utilizes membranes prepared from NIH 3T3 cells which express human CCR5 chemokine receptor. RANTES (Regulated upon Activation, Normal T cell Expressed and Secreted) is a natural ligand for the CCR5. In a 96-well plate format, 14 ug (total protein) of membrane preparation and 0.05 nM of $^{125}$I Rantes are incubated in the presence (and absence) of compound for one hour. Compound II is serially diluted over a range of 0.001 ug/ml to 1.0 ug/ml and each concentration is tested in replicates of four. Reaction cocktails are harvested through glass fiber filters, and washed thoroughly. Total counts for replicates are averaged and 50 percent inhibition of total membrane binding of $^{125}$I Rantes is determined. Compound of formula II demonstrated an IC$_{50}$ value of 78.6 nM for II. A similar range of activity is expected for compounds of formulas I and III.

TABLE 3

$^{13}$C NMR Data of Compounds of Formulas I, II & III[a]

| Carbon # | I | II | III |
|---|---|---|---|
| 1 | 45.8d[b] | 46.9d | 45.2d |
| 2 | 47.8 d | 48.5d | 48.7d |
| 3 | 128.4 d | 129.4d | 126.2d |
| 4 | 133.5 d | 134.5d | 134.3d |
| 5 | 40.4 d | 41.2d | 38.4d |
| 6 | 41.8 t | 42.6 t | 42.4 t |
| 7 | 32.4 d | 33.2d | 33.2d |
| 8 | 45.8 t | 46.6 t | 46.8d |
| 9 | 39.1 d | 39.9d | 35.1d |
| 10 | 46.0 d | 46.9d | 39.9d |
| 11 | 135.3 s | 136.2 s | 138.2 s |
| 12 | 15.1 q | 16.8q | 16.5q |
| 13 | 121.5 d | 122.3d | 122.0d |
| 14 | 12.9 q | 13.8q | 13.8q |
| 15 | 21.8 q | 22.6q | 22.8q |
| 16 | 20.5 q | 21.4q | 20.2q |
| 17 | 192.8 s | 193.5 s | 192.9 s |
| 18 | 100.6 s | 101.4 s | 100.9 s |
| 19 | 194.8 s | 194.9 s | 194.7 s |
| 20 | 58.9 d | 60.9d | 60.7d |
| 21 | 175.6 s | 176.6 s | 176.6 s |
| 22 | 41.3 t | 42.7 t | 43.0 t |
| 23 | 72.9 s | 75.1 s | 75.3 s |
| 24 | 25.0 q | 27.7q | 28.0q |
| 25 | 176.9 s | 177.2 s | 176.9 s |
| 25OCH$_3$ | — | — | 52.9q |

[a]Recorded at 100 MHz in acetone-d$_6$, chemical shifts in ppm from TMS.
[b]Multiplicity was determined by APT data.

TABLE 4

Crystallographic Data[1]

| | |
|---|---|
| Molecular formula | C$_{25}$H$_{35}$NO$_6$ |
| Formula weight | 445.56 |
| Crystal system | monoclinic |
| Space group | P2$_1$(C$_2^2$)-No. 4 |
| a (Å) | 21.569 (3) |
| b (Å) | 6.396 (1) |
| c (Å) | 9.038 (1) |
| β (°) | 98.78 (1) |
| V (Å) | 1232.2 (5) |
| Z | 2 |
| D$_{calcd.}$ (g cm$^{-3}$) | 1.201 |
| Radiation (λ, Å) | Cu-Kα (1.5418) |
| Absorption coefficient, μ(cm$^{-1}$) | 6.6 |
| Temp. (° C.) | 25 |
| Crystal dimensions (mm) | 0.12 × 0.20 × 0.04 |
| Scan type | ω-2θ |
| Scanwidth(°) | 0.80 + 0.14tanθ |
| θ$_{max}$(°) | 75 |
| Intensity control refls.; variation; repeat time (hr) | 301, 1–10, −3–11, 8–11; <1.0%; 2 |
| Total no. of non-equiv. refls. | 2758 |

TABLE 4-continued

Crystallographic Data[1]

| (±h, −k + l) recorded | |
|---|---|
| No. of refls. retained [>2.0σ(I)] | 1006 |
| No. of parameters refined | 289 |
| Extinction correction | 1.0 (5) × 10$^{-6}$ |
| R (R$_w$)[2] | 0.051 (0.063) |
| Goodness-of-fit[3] | 1.36 |
| Max. shift:esd in final least-squares cycle | 0.03 |
| Final Δρ(e/Å$^3$) max; min. | 0.16; −0.18 |

[1]An Enraf-Nonius CADA diffractmer (Cu-Kα radiation, graphite monochromator) was used for all measurements. intensity data were corrected for the usual Lorentz and polarization effects. Laue symmetry indicated that the crystals belonged to the monoclinic system. The space group was determined from the systematic absences and the fact that the molecule is chiral. Final unit-cell parameters were calculated from the diffractometer setting angles for 25reflections (25° < θ < 29°) widely separated in reciprocal space.

The crystal structure was solved by direct methods (MULTAN11/82). Approximate coordinates for the non-hydrogen atoms were obtained in part from an E-map and from a series of weighted F° Fourier syntheses phased successively by an increasing number of atoms. Positional and thermal parameters (first isotropic and then anisotropic) of these atoms were adjusted by means of several rounds of full-matrix least-squares calculations. The majority of hydrogen atoms were located in difference Fourier syntheses and were incorporated at their calculated positions in the subsequent least-squares iterations. An extinction correction was included as a variable in the later cycles. A final difference Fourier synthesis contained no unusual features.

Crystallographic calculations were performed on PDP11/44 and MicroVAX computers by use of the Enraf-Nonius Structure Determination Package (SDP). For all structure-factor calculations, neutral atom scattering factors and their anomalous dispersion corrections were taken from *International Tables for X-Ray Crystallography*, vol. IV, The Kynoch Press, Birmingham, U.K., 1974.

[2]$R=\Sigma||F°|-F_c||/\Sigma|F°|;R_w=[\Sigma w(|F°|-|F_c|)^2/\Sigma w|F°|^2]^{1/2};\Sigma w\Delta^2[w=1\sigma^2(|F°|),\Delta=(|F°||F_c|)]$ was minimized.

[3]Goodness-of-fit=$[\Sigma w\Delta^2/(N_{observations}-N_{parameters})]^{1/2}$

What is claimed is:
1. A compound represented by the formula I or II or III:

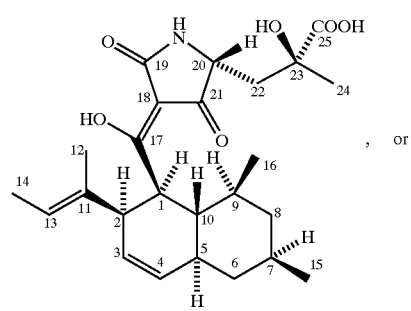

I

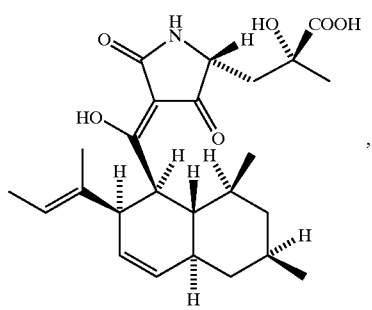

II

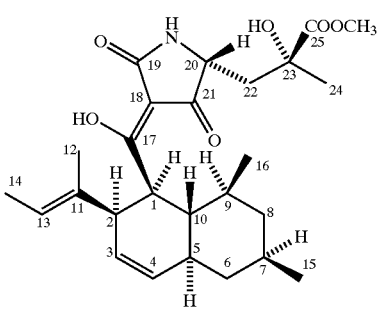

III in substantially chemically pure form, or a pharmaceutically acceptable salt thereof.

2. A pharmaceutical composition comprising a CCR5 antagonist effective amount of a compound of claim 1 and at least one pharmaceutically acceptable carrier.

3. A method of treating patients having a HIV-1 infection by administering a therapeutically effective amount of a compound of formula I or II or III of claim 1 sufficient to lower HIV-1-RNA.

4. A method of treating patients having a HIV-1 infection by administering a therapeutically effective amount of HAART in association with a therapeutically effective amount of a compound of formula I or II or III of claim 1 sufficient to lower HIV-1-RNA.

5. A method of treating patients having a HIV-1 infection by administering a therapeutically effective amount of pegylated interferon-alfa in association with a therapeutically effective amount of a compound of formula I or II or III of claim 1 sufficient to lower HIV-1-RNA wherein the pegylated interferon-alfa is pegylated interferon-alpha 2a or pegylated interferon-alpha 2b.

6. A method of treating pediatric patients having a HIV-1 infection which comprises administering a therapeutically effective amount of pegylated interferon-alfa in association with a therapeutically effective amount of a CCR5 antagonist represented by the structural formula I or II or III of claim 1 wherein the pegylated interferon-alfa is pegylated interferon-alpha 2a or pegylated interferon-alpha 2b.

7. A method of treating patients co-infected with HIV-1 and HCV which comprises administering a therapeutically effective amount of pegylated interferon-alfa in association with a therapeutically effective amount of ribavirin and a therapeutically effective amount of HAART and a therapeutically effective amount of a CCR5 antagonist represented by the structural formula I or II or III of claim 1 wherein the pegylated interferon-alfa is pegylated interferon-alpha 2a or pegylated interferon-alpha 2b.

8. A CCR-5 active complex comprising the compounds represented by formulas I, II and III of claim 1.

* * * * *